US00PP21675P2

(12) United States Plant Patent
Sakazaki

(10) Patent No.: US PP21,675 P2
(45) Date of Patent: Jan. 25, 2011

(54) ***PETUNIA* PLANT NAMED 'USTUN19603'**

(50) Latin Name: *Petunia×hybrida*
Varietal Denomination: USTUN19603

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/590,817

(22) Filed: Nov. 14, 2009

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent L Bell
(74) *Attorney, Agent, or Firm*—C. A. Whealy

(57) ABSTRACT

A new and distinct cultivar of *Petunia* plant named 'USTUN19603', characterized by its upright, outwardly spreading and low mounding plant habit; freely branching and vigorous growth habit; early and freely flowering habit; small flowers that are bright pink in color; and good garden and summer performance.

1 Drawing Sheet

Botanical designation: *Petunia×hybrida.*
Cultivar denomination: 'USTUN19603'.

BACKGROUND OF THE INVENTION

The present invention relates to a new and distinct cultivar of *Petunia* plant, botanically known as *Petunia×hybrida* and hereinafter referred to by the name 'USTUN19603'.

The new *Petunia* plant is a product of a planned breeding program conducted by the Inventor in Higashiomi, Shiga, Japan and Bonsall, Calif. The objective of the breeding program is to create new *Petunia* plants with compact plant habit, freely branching growth habit, early flowering, attractive small flowers and good summer performance.

The new *Petunia* plant originated from a cross-pollination made by the Inventor on May 14, 2004 in Hikone, Shiga, Japan of *Petunia×hybrida* 'Little Holiday Pink', not patented, as the female, or seed, parent with *Petunia×hybrida* 'Blue Frill Pink', disclosed in U.S. Plant Pat. No. 18,153, as the male, or pollen, parent. The new *Petunia* plant was discovered and selected by the Inventor as a single flowering plant within the progeny of the stated cross-pollination in a controlled environment in Bonsall, Calif. on May 26, 2005.

Asexual reproduction of the new *Petunia* plant by vegetative cuttings in a controlled greenhouse environment in Bonsall, Calif. since May 30, 2005, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USTUN19603' . These characteristics in combination distinguish 'USTUN19603' as a new and distinct cultivar of *Petunia:*

1. Upright, outwardly spreading and low mounding plant habit.
2. Freely branching and vigorous growth habit.
3. Early and freely flowering habit.
4. Small flowers that are bright pink in color.
5. Good garden and summer performance.

Plants of the new *Petunia* differ from plants of the female parent, 'Little Holiday Pink', primarily in flower color as plants of 'Little Holiday Pink' have darker pink-colored flowers. In addition, plants of the new *Petunia* are more outwardly spreading than plants of 'Little Holiday Pink'.

Plants of the new *Petunia* differ from plants of the male parent, 'Blue Frill Pink', primarily in flower color and petal appearance as plants of 'Blue Frill Pink' have more lavender-colored flowers with petals that are more ruffled. In addition, plants of the new *Petunia* are not as outwardly spreading as plants of 'Blue Frill Pink'.

Plants of the new *Petunia* can be compared to plants of 'Horizon Lavender', not patented. In side-by-side comparisons, plants of the new *Petunia* differed from plants of 'Horizon Lavender' in the following characteristics:

1. Plants of the new *Petunia* had smaller flowers than plants of 'Horizon Lavender'.
2. Plants of the new *Petunia* and 'Horizon Lavender' differed in flower color as plants of 'Horizon Lavender' had darker-colored flowers.

Plants of the new *Petunia* can also be compared to plants of 'Mediopimo', disclosed in U.S. Plant Pat. No. 14,858. In side-by-side comparisons, plants of the new *Petunia* differed from plants of 'Mediopimo' in the following characteristics:

1. Plants of the new *Petunia* were more compact than plants of 'Mediopimo'.
2. Plants of the new *Petunia* had smaller flowers than plants of 'Mediopimo'.
3. Plants of the new *Petunia* and 'Mediopimo' differed in flower color as plants of 'Mediopimo' had darker-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN19603' grown in a container.

The photograph at the top of the sheet is a close-up view of typical flowers and leaves of 'USTUN19603'.

DETAILED BOTANICAL DESCRIPTION

The aforementioned photographs and following observations, measurements and values describe plants grown in Bonsall, Calif., under commercial practice during the summer and early autumn in an outdoor nursery with day temperatures ranging from 18° C. to 38° C. and night temperatures ranging from 9° C. to 18° C. Plants were pinched one time and were six weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN19603'.

Parentage:

*Female, or seed, parent.*—*Petunia×hybrida* 'Little Holiday Pink', not patented.

*Male, or pollen, parent.*—*Petunia×hybrida* 'Blue Frill Pink', disclosed in U.S. Plant Pat. No. 18,153.

Propagation:

*Type.*—Terminal vegetative cuttings.

*Time to produce a rooted young plant, summer.*—About 15 days at air temperatures of 29° C. and soil temperatures of 17° C.

*Time to produce a rooted young plant, winter.*—About 20 days at air temperatures of 21° C. and soil temperatures of 17° C.

*Root description.*—Medium in thickness; white in color.

*Rooting habit.*—Freely branching; moderately dense.

Plant description:

*Plant and growth habit.*—Annual flowering plant; upright, outwardly spreading and low mounding plant habit; vigorous growth habit; freely branching habit with about 25 lateral branches and numerous secondary and tertiary lateral branches per plant; pinching enhances development of lateral branches.

*Plant height.*—About 10 cm.

*Plant diameter* (*area of spread*).—About 41 cm.

*Lateral branches.*—Length: About 28 cm. Diameter: About 2 mm. Internode length: About 1 cm. Strength: Strong. Texture: Pubescent; viscid. Color: Close to 145A.

Foliage description:

*Arrangement.*—Alternate before flowering; opposite after flowers develop; simple.

*Length.*—About 3.4 cm.

*Width.*—About 1.7 cm.

*Shape.*—Elliptical.

*Apex.*—Acute.

*Base.*—Attenuate.

*Margin.*—Entire.

*Texture, upper and lower surfaces.*—Pubescent; viscid.

*Venation pattern.*—Pinnate, arcuate.

*Color.*—Developing leaves, upper surface: Close to 138A. Developing leaves, lower surface: Close to 147B. Fully expanded leaves, upper surface: Close to 137B; venation, close to 147B. Fully expanded leaves, lower surface: Close to 146A; venation, close to 146B.

*Petioles.*—Length: About 7 mm. Diameter: About 2 mm. Texture, upper and lower surfaces: Pubescent. Color, upper surface: Close to 144B. Color, lower surface: Close to 146D.

Flower description:

*Flower type and habit.*—Single axillary salverform flowers; flowers face mostly upward or outward; freely flowering habit, about 21 to 24 flower buds and open flowers per lateral branch.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About three to five days; flowers persistent.

*Fragrance.*—Faint; sweet.

*Flower size.*—Diameter: About 2.8 cm. Depth (height): About 3 cm. Tube length: About 2.2 cm. Throat diameter, distal end: About 6 mm. Tube diameter, proximal end: About 2 mm.

*Flower buds.*—Length: About 2.4 cm. Diameter: About 5 mm. Shape: Elongated oblong. Color: Close to 56D.

*Petals.*—Quantity/arrangement: About five petals fused in a single whorl, funnelform. Petal lobe length (from throat): About 1.2 cm. Petal lobe width: About 1.3 cm. Petal lobe shape: Roughly fan-shaped. Petal lobe apex: Acute with a small central point. Petal lobe margin: Entire. Petal lobe texture, upper and lower surfaces: Smooth, glabrous; velvety. Throat texture: Smooth, glabrous. Tube texture: Pubescent. Color: When opening, upper surface: Close to 186C. When opening, lower surface: Close to 65D. Fully opened, upper surface: Close to N74C; towards the throat, close to 75B to 75C; venation, close to N74C. Fully opened, lower surface: Close to 84D; venation, close to 146D. Flower throat: Close to 75C to 75D; venation, close to 145C. Flower tube (outside): Close to 76D; venation, close to 146D.

*Sepals.*—Arrangement/appearance: Single whorl of five sepals fused at base, star-shaped calyx. Length: About 1.2 cm. Width: About 2 mm. Shape: Lanceolate. Apex: Broadly acute. Margin: Entire. Texture, upper and lower surfaces: Pubescent. Color, upper surface: Close to 146A. Color, lower surface: Close to 146A to 146B.

*Peduncles.*—Length: About 2 cm. Width: About 1 mm. Angle: About 45° to 60° from the stem axis. Strength: Moderately strong. Texture: Pubescent. Color: Close to 144B.

*Reproductive organs.*—Stamens: Quantity per flower: Five. Filament length: About 1.8 cm to 2 cm. Filament color: Close to 157D. Anther shape: Oval. Anther length: About 1.5 mm. Anther color: Close to 156C. Pollen amount: Scarce. Pollen color: Close to 196A. Pistils: Quantity per flower: One. Pistil length: About 1.7 cm. Style length: About 1.3 cm. Style color: Close to 145C. Stigma shape: Rounded anvil-shaped. Stigma color: Close to 145A. Ovary color: Close to 144A.

*Seed/fruit.*—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden and summer performance and have been observed to tolerate rain, wind and temperatures ranging from about 0° C. to about 40° C.

It is claimed:

1. A new and distinct *Petunia* plant named 'USTUN19603' as illustrated and described.

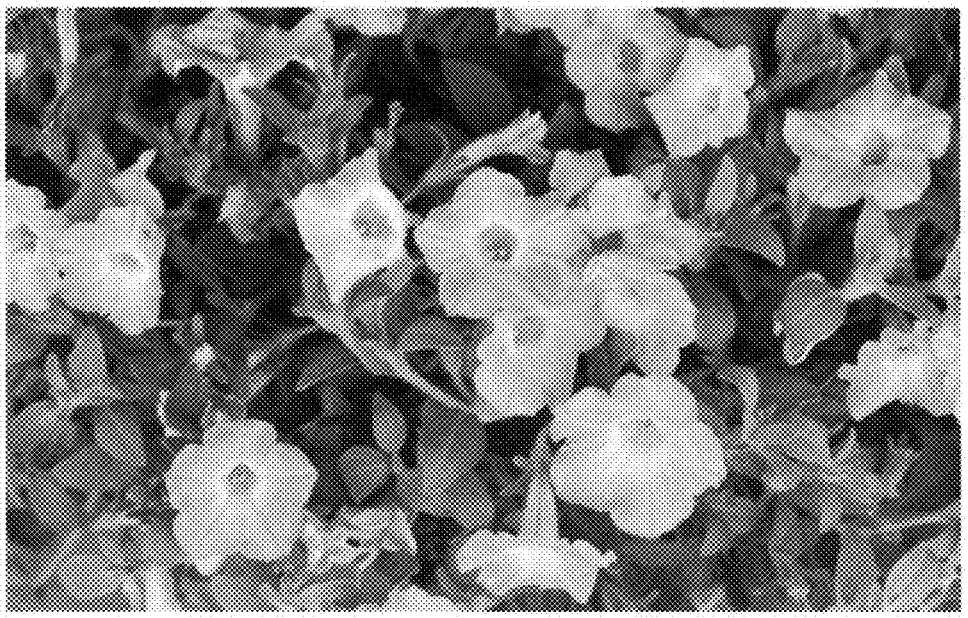
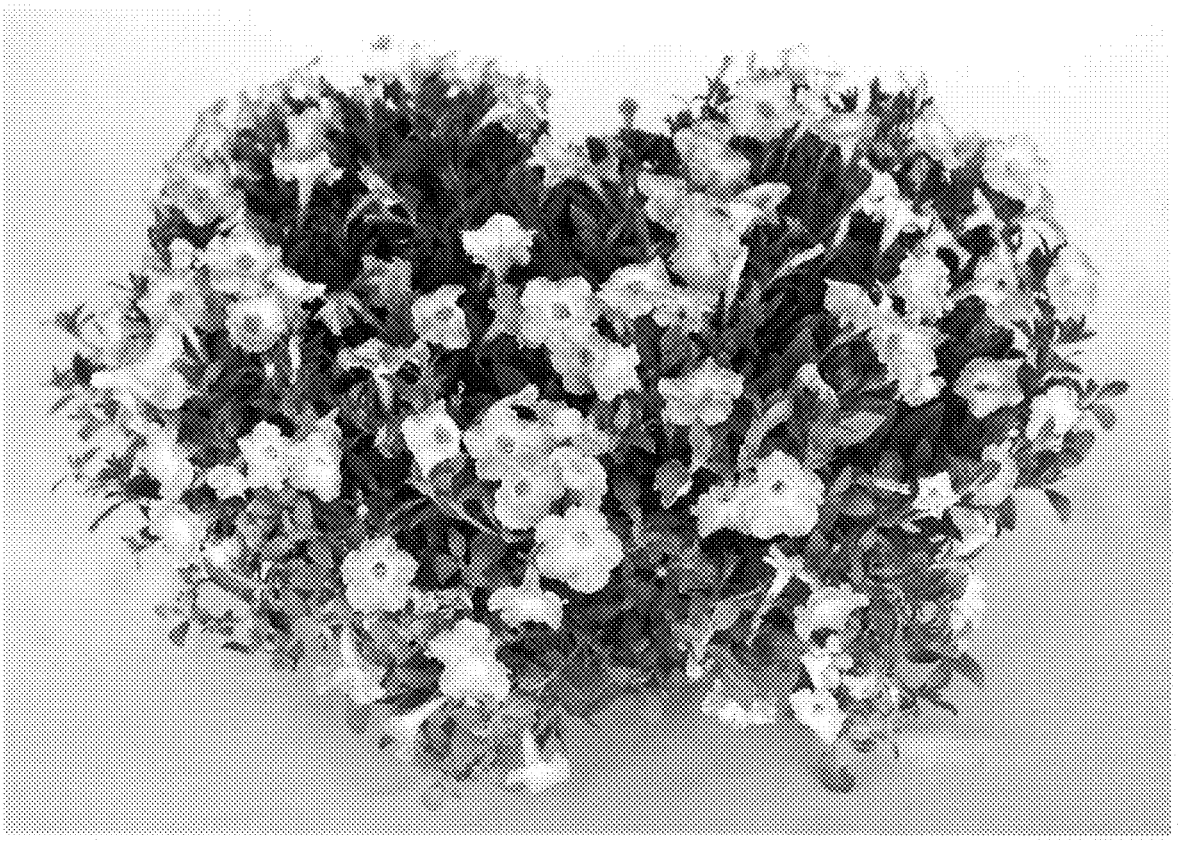

* * * * *